US00RE38362E

(19) United States
(12) Reissued Patent
Collin et al.

(10) Patent Number: US RE38,362 E
(45) Date of Reissued Patent: Dec. 23, 2003

(54) COMPOSITIONS FOR MAKING UP THE EYES

(75) Inventors: Natalie Collin, Sceaux (FR); Huguette Couture, Vigneux sur Seine (FR)

(73) Assignee: L'Oreal, Paris (FR)

(21) Appl. No.: 09/452,377

(22) Filed: Dec. 1, 1999

Related U.S. Patent Documents

Reissue of:
(64) Patent No.: 5,876,704
Issued: Mar. 2, 1999
Appl. No.: 08/941,271
Filed: Sep. 30, 1997

(30) Foreign Application Priority Data

Sep. 30, 1996 (FR) ..... 96-11878

(51) Int. Cl.[7] ..... A61K 7/032
(52) U.S. Cl. ..... 424/63; 424/70.7; 424/70.11; 424/70.12; 424/70.15; 424/70.16; 424/401; 424/78.3
(58) Field of Search ..... 424/63, 70.7, 401, 424/70.11, 70.12, 70.15, 70.16, 78.03

(56) References Cited

U.S. PATENT DOCUMENTS

| | | | | |
|---|---|---|---|---|
| 4,963,348 A | * | 10/1990 | Bolich | 424/71 |
| 5,104,642 A | * | 4/1992 | Wells | 424/47 |
| 5,120,531 A | * | 6/1992 | Wells | 424/70 |
| 5,620,693 A | | 4/1997 | Piot | |
| 5,626,853 A | | 5/1997 | Bara | |
| 6,024,946 A | | 2/2000 | Dubief et al. | |

FOREIGN PATENT DOCUMENTS

| | | | |
|---|---|---|---|
| EP | 0214626 | * | 5/1988 |
| EP | 0266921 | * | 5/1988 |
| EP | 0424260 | * | 4/1991 |
| EP | 0 610 026 | | 8/1994 |
| EP | 0 687 461 | | 12/1995 |
| GB | 2114580 | * | 8/1983 |
| JP | 4-210 613 | | 7/1992 |
| WO | 91 12793 | | 9/1991 |
| WO | 94 17775 | | 8/1994 |
| WO | 95 15741 | | 6/1995 |
| WO | 96 36323 | | 11/1997 |

* cited by examiner

*Primary Examiner*—Edward J. Webman
(74) *Attorney, Agent, or Firm*—Oblon, Spivak, McClelland, Maier & Neustadt, P.C.

(57) ABSTRACT

Cosmetic composition, in particular one for making up the eyes, comprising:

(a) at least one aqueous phase comprising at least one film-forming polymer, (b) at least one fatty phase comprising at least one wax, and (c) at least one silicone selected from the group consisting of:

(i) oxyalkylenated silicones, and (ii) linear polysiloxane-polyoxyalkylene block copolymers.

25 Claims, No Drawings

COMPOSITIONS FOR MAKING UP THE EYES

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to a composition, in particular one for making up the eyes, comprising oxyalkylenated silicone derivatives. These compositions have improved cosmetic properties, in particular of staying power.

2. Description of the Background

Many mascara formulations exist on the market. However, the consumer still expects an improvement in the properties of these mascaras, namely the lengthening of the eyelash, better adhesion of the composition to the eyelash, better shaping, also referred to as weighting, of the eyelashes, better staying power of the make-up over time and better resistance to mechanical stresses. For example, some users wish to be able to keep the same make-up on for the day and the evening. It is also known that rubbing the fingers on the eyelids and the contact of spectacles with the eyelashes tend to crumble the mascara away. In particular, the presence of pigments and/or fillers in compositions for making up the eyelashes makes these compositions particularly subject to crumbling. The compositions known to date have not solved these problems satisfactorily.

The object of the present invention is to provide a composition, in particular one for making up the eyes, which dries rapidly and has improved properties of lengthening and weighting of the eyelashes, of staying power and of mechanical strength.

SUMMARY OF THE INVENTION

The object of the invention is met by a cosmetic composition, in particular one for making up the eyelashes, comprising:

(a) at least one aqueous phase comprising at least one film-forming polymer, (b) at least one fatty phase comprising at least one wax, and (c) at least one silicone selected from the group consisting of:

(i) oxyalkylenated silicones, and (ii) linear polysiloxane-polyoxyalkylene block copolymers The object of the invention is also met by the use of a composition as defined above for the production of a make-up having better staying power over time and/or improved weighting and/or better resistance to crumbling and/or better lengthening of the eyelashes and/or an improved rate of drying.

The object of the invention is also met by the use of a silicone selected from the group consisting of:

(i) oxyalkylenated silicones, and (ii) linear polysiloxane-polyoxyalkylene block copolymers, in a cosmetic composition, in particular one for making up the eyes, comprising:

(a) at least one aqueous phase comprising al least one film-forming polymer, and (b) at least one fatty phase comprising at least one wax, to impart to this composition better staying power over time and/or improved weighting and/or better resistance to crumbling and/or better lengthening of the eyelashes and/or an improved rate of drying.

These compositions are preferably in the form of an emulsion of the fatty phase in the aqueous phase or a dispersion of the aqueous phase in the fatty phase.

DETAILED DESCRIPTION OF THE INVENTION

Hitherto, dimethicone copolyols were known in various applications: as an emulsifying agent in compositions of the water-in-oil type, or alternatively as a plasticizer in hairstyling products. For example, EP-A-705,595, describes hairstyling compositions comprising a plasticizer, which may be a dimethicone copolyol or a polycarboxylic acid, in order to improve the flexibility of fixing resins.

However, the compositions described in EP-A-705,595, are very different in terms of their structure from compositions for making up the eyes. In particular, these compositions contain neither pigments nor fillers, nor do they contain large amounts of waxes. On reading that document, nothing would lead a person skilled in the art to think that the properties of lengthening of the eyelash, of adhesion to the eyelash, of weighting of the eyelashes, of staying power of the make-up and of resistance of the mascaras to mechanical stresses could he improved in a spectacular manner by the use of dimethicone copolyols.

The compositions according to the invention also advantageously contain at least one pigment, which may be selected from inorganic, organic and optionally pearlescent pigments. These pigments are preferably included in a proportion ranging from 0.25 to 25%, preferably from 1 to 20%, by weight relative to the total weight of the composition, depending on the coloration and intensity of the coloration which it is desired to obtain. Among the pigments which can be used include the oxides of zinc, of iron or of chromium, ferric blue, carbon black and the lakes commonly employed which ate salts of acidic dyes.

The composition according to the invention thus comprises a silicone which may be an oxyalkylenated silicone.

Preferably, the oxyalkylenated silicones do not have $C_8$–$C_{22}$ alkoxy or alkyl radical linked directly to a silicon atom.

The oxyalkylenated silicones are selected from compounds of general formula (I), also referred to as dimethicone copolyols:

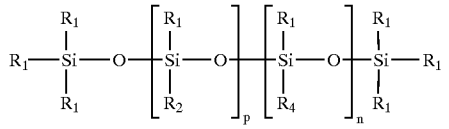

(I)

in which formula:

$R_1$ and $R_4$, which are identical or different, represent a hydrogen atom, a linear or branched $C_1$–$C_{30}$ alkyl radical or a phenyl radical, $R_2$, which are identical or different, represent $—(C_xH_{2x})—(OC_2H_4)_a—(OC_3H_6)_b—OR_3$, $R_3$, which are identical or differed, are chosen from a hydrogen atom, a linear or branched alkyl radical having from 1 to 12 carbon atoms, or a linear or branched aryl radical having from 2 to 12 carbon atoms, o ranges from 0 to 1000, p ranges from 1 to 30, a ranges from 0 to 50, b ranges from 0 to 50, a+b is greater than or equal to 1, x ranges from 1 to 5, the number-average molecular weight being greater than or equal to 15,000 and preferably between 25,000 and 75,000.

Preferably, $R_4$ is not hydrophobic, and preferably not a $C_8$–$C_{22}$ alkyl radical.

Preferably, oxyalkylenated silicones of general formula (I) are used which satisfy at least one, and preferably all, of the following conditions:

$R_1$ and $R_4$ denote a methyl radical, $R_3$ represents a hydrogen atom, a methyl radical or an acetyl radical, and preferably hydrogen, p ranges from 8 to 20, a is between 5 and 40 and preferably between 15 and 30, b is between 5 and 40 and preferably between 15 and 30, x is equal to 2 or 3, n ranges from 20 to 600, preferably from 50 to 500 and even more preferably from 100 to 300.

Such silicones are described, for example, in U.S. Pat. No. 4,311,695, which is hereby incorporated by reference.

Dimethicone copolyols have been presented in particular by the company Dow Corning during the 17th International Congress of the I.F.S.C.C, of October 1992 and have been reported in the article "Water-soluble dimethicone copolyol waxes for personal care industry" by Linda Madore et al., pages 1 to 3.

These dimethicone copolyols me water-soluble polydimethylsiloxanes (PDMS) containing one or more ether functions (oxyalkylene, in particular oxyethylene and/or oxypropylene).

Such dimethicone copolyols are sold in particular by the company Goldschmidt under the name Abil B8851 or Abil B88183. Mention may also be made of compounds KF 351 to 354 and RF 615 A sold by the company Shin Etsu or DMC 6038 from the company Wacker.

The dimethicone copolyol derivatives which can be used in the invention are, in particular, dimethicone copolyols containing a phosphate, sulphate, propyldimethylammonium myristamide chloride, stearate, amine, glycomodified, etc, group. The compounds sold by the company Siltech under the name Silphos A100, Siltech amine 65, Silwax WDIS, myristamide silicone quat, or by the company Phoenix under the name Pecosil PS 100 may be used in particular as dimethicone copolyol derivatives.

It is also possible to use the derivatives sold by the company Wacker under the name VP 1661, or by the company Dow Corning under the name 2501 cosmetic wax.

The silicones most particularly preferred are, for example, those sold by the company Dow Corning under the trade name Q2-5220 and by the company Rhone-Poulenc under the name Mirasil DMCO.

When, in the context of the present invention, linear polysiloxane-polyoxyalkylene block copolymers me used, these preferably have the general formula (II) below:

$$(\{Y(R_2SiO)_{a'}.R'_2SiYO\}\{(C_{n'}.H_{2n'}.O)_{b'}.\})_{c'} \quad \text{(II)}$$

in which:

R and R', which are identical or different, represent a monovalent hydrocarbon radical containing no aliphatic unsaturation, n' is an integer between 2 and 4, a' is an integer greater than or equal to 5, b' is an integer greater than or equal to 4, c' is an integer greater than or equal to 4, Y represents a divalent organic group which is attached to the adjacent silicon atom by a carbon silicon bond and to a polyoxyalkylene block by an oxygen atom, the number average molecular weight of each siloxane block is between about 400 and about 10,000, and that of each polyoxyalkylene block being between about 300 and about 10,000, the siloxane blocks represent from about 10% to about 90% by weight of the block copolymer, the number average molecular weight of the block copolymer being at least 3000.

The radicals R and R' are more preferably selected from the group consisting of alkyl radicals such as, for example, methyl, ethyl, propyl, butyl, pentyl, hexyl, octyl, decyl and dodecyl radicals; aryl radicals such as, for example, phenyl and naphthyl radicals; aralkyl radicals such as, for example. benzyl and phenylethyl; tolyl, xylyl and cyclohexyl radicals.

The divalent radical Y is preferably —R"—, —R"—CO—, —R"—NHCO—. —R"—NH—CO—NH—R'"—NHCO or —R"—OCONH—R'"—NHCO—, where R" is a divalent alkylene group such as, for example, ethylene, propylene or butylene and R'" is a divalent alkylene group or a divalent arylene group such as $—C_6H_4—$, $—C_6H_4—C_6H_4—$, $C_6H_4—CH_2—C_6H_4—$or $—C_6H_4—CH(CH_3)_2—C_6H_4—$.

Even more preferably, Y represents a divalent alkylene radical and more particularly the $—CH_2—CH_2—CH_2$radical.

The preparation of the block copolymers used in the context of the present invention is described in particular in European application EP 0,492657 A1.

According to a specific embodiment of the invention, the block copolymer is selected from the following copolymers:

$$\{\{(CH_3)_2SiO\}_{41}(CH_3)_2SiCH_2CH(CH_3)CH_2—O(C_2H_4O)_{18}—(C_3H_6O)_{33}CH_2CH(CH_3)CH_2\}_{16.1}$$

$$\{\{(CH_3)_2SiO\}_{31}(CH_3)_2SiCH_2CH(CH_3)CH_2—O(C_2H_4O)_{20}—(C_3H_6O)_{29}CH_2CH(CH_3)CH_2\}_{13.3}$$

$$\{\{(CH_3)_2SiO\}_{9}(CH_3)_2SiCH_2CH(CH_3)CH_2—O(C_2H_4O)_{20}—(C_3H_6O)_{29}CH_2CH(CH_3)CH_2\}_{26.3}$$

$$\{\{(CH_3)_2SiO\}_{16}(CH_3)_2SiCH_2CH(CH_3)CH_2—O(C_2H_4O)_{18}—(C_3H_6O)_{20}CH_2CH(CH_3)CH_2\}_{21.5}$$

$$\{\{(CH_3)_2SiO\}_{9}(CH_3)_2SiCH_2CH(CH_3)CH_2—O(C_2H_4O)_{5}—(CH_2CH(CH_3)CH_2\}_{4.8}$$

The silicones used in the compositions of the invention may be water-soluble or liposoluble. Depending on their water- or liposolubility, they are introduced, respectively, into the aqueous phase or the fatty phase.

The waxes which can be used in the composition according to the invention generally possess a melting point of between 40° and 110° C, and have a needle penetration, at 25° C., of between 3 and 40, as measured according to US standard ASTM D 5 or according to French standard NFT 004. The principle for measuring the penetration of a needle according to the standards ASTM D 5 and AFT 004 consists in measuring the depth, expressed in tenths of a millimeter, to which a standardized needle which weighs 2.5 g penetrates when placed in a needle holder weighing 47.5 g, i.e. a total of 50 g, the needle being placed on the wax for 5 seconds.

The waxes which can be used in the present invention me selected from animal waxes, plant waxes, mineral waxes, synthetic waxes and various fractions of natural waxes, all of the waxes having the two physical characteristics mentioned above.

Included among the animal waxes are beeswaxes, lanolin waxes and Chinese insect waxes.

Among the plant waxes are rice waxes, carnauba waxes, candelilla waxes, ouricurry waxes, cork fibre waxes, sugarcane waxes. Japan waxes, sumach wax and cotton wax.

Among the mineral waxes are paraffins, microcrystalline waxes. Montan waxes and ozokerites.

Among the synthetic waxes which can be used in particular are polyethylene waxes, waxes obtained by Fischer-Tropsch synthesis, waxy copolymers and esters thereof, and silicone waxes.

It is also possible to use hydrogenated animal or plant oils which still satisfy the two physical characteristics mentioned above.

Among these oils are hydrogenated jojoba waxes and hydrogenated oils which are obtained by catalytic hydrogenation of fatty substances composed of a linear or non-linear $C_8$—$C_{32}$ fatty chain, hydrogenated sunflower oil, hydrogenated castor oil, hydrogenated coconut oil, hydrogenated lanolin and hydrogenated palm oils.

The waxes which can be used according to the present invention are preferably solid and rigid at a temperature below 50° C.

These waxes may be in the form of stable dispersions of colloid particles of wax as may be prepared according to known methods, such as "Microemulsions Theory and Practice". L. M. Prince Ed., Academic Press (1977), pages 21–32.

Advantageously, the compositions according to the invention comprise from 6 to 40% wax, by weight relative to the total weight of the composition, preferably from 10 to 25%.

The composition according to the invention also comprises at least one film-forming polymer, in solution, optionally in colloidal solution or colloidal dispersion.

The film-forming polymer is used in amounts which make it possible to obtain good adhesion of the composition to the eyelash, and lengthening, coating and curving which give a wide-eyed impression, the eyelashes being well separated.

The compositions according to the invention preferably comprise an amount of film-forming polymer ranging from 0.1 to 25% by weight relative to the total weight of the composition. The compositions which form the subject of the present invention advantageously comprise an amount ranging from 1 to 10%, by weight relative to the total weight of the composition, of film-forming polymer.

The film-forming polymer may be selected from:

keratin derivatives, such as keratin hydrolysates and sulphonic keratins;

anionic, cationic, amphoteric or nonionic chitin or chitosan derivatives;

cellulose derivatives such as hydroxyethylcellulose, hydroxypropylcellulose, methylcellulose, ethylhydroxyethylcellulose and carboxymethylcellulose, as well as quaternized derivatives of cellulose;

acrylic polymers or copolymers, such as polyacrylates a polymethacrylates;

polyvinylpyrrolidones and vinyl copolymers, such as copolymers of methyl vinyl ether and of malic anhydride or the copolymer of vinyl acetate and of crotonic acid;

anionic polyester and/or polyesteramide polymers capable of forming solutions, optionally colloidal solutions or colloidal dispersions, in water, these polymers comprising monomers bearing a function: —$SO_3M$, with M representing a hydrogen atom, an ammonium ion $NH_4^+$or a metal ion, for example an $Na^+$, $Li^+$, $K^+$, $Mg^{2+}$, $Ca^{2+}$, $Cu^{2+}$, $Fe^{2+}$ or $Fe^{3+}$ ion. Preferred are the polymers described in U.S. Pat. Nos. 3,734,874; 4,233,196; and 4,304,901. Film-forming polyester polymers based on at least one dicarboxylic acid, on at least one diol and at least one difunctional aromatic monomer also bearing a group —$SO_3M$ as described above are advantageously selected;

polymers of natural origin, which are optionally modified, such as:

gum arabics, guar gum, xanthan derivatives, karaya gum;

alginates and carrageenates;

glycoaminoglycans, hyaluronic acid and derivatives thereof;

shellac resin, sandarac, dammar resins, elemi gums and copal resins.

The compositions according to the invention preferably comprise from 0.01 to 5% of silicone, even more preferably from 0.4 to 1.5%, by weight relative to the total weight of the composition. The compositions according to the invention advantageously comprise from 10 to 30% by weight of silicone relative to the total weight of the film-forming polymer.

The components of the oily and aqueous phases may be independently dissolved or melted at a temperature of 85° C. and then mixed together.

The composition according to the present invention may be in the form of an oil-in-water emulsion or a water-in-wax dispersion.

When it is used in the form of an oil-in-water emulsion, the composition may contain emulsifying surfactants present in a proportion of between 2 and 30% by weight relative to the total weight of the composition. These surfactants may be selected from anionic or nonionic surfactants. Reference may be made to "Encyclopedia of Chemical Technology. Kirk-Othmer" volume 22, p.333–432, 3rd edition, 1979. Wiley, for the definition of the properties and (emulsifying) functions of the surfactants, in particular p347–377 of this reference, for the anionic and nonionic surfactants.

The surfactants preferably used in the compositions according to the invention are:

among the nonionic surfactants: fatty acids, fatty alcohols. polyethoxylated or polyglycerolated fatty alcohols such as polyethoxylated stearyl or cetyl stearyl alcohols, fatty acid esters of sucrose, alkyl glucose esters, in particular polyoxyethylenated fatty esters of $C_1$—$C_6$-alkyl glucose.

among the anionic surfactants: amine stearates.

When the composition according to the invention is in the form of an oil-in-water emulsion, the water advantageously represents from 30 to 80% by weight of the total weight of the composition.

When the composition according to the invention is in the form of a water-in-wax dispersion, it also preferably comprises at least one thickener and at least one volatile solvent or organic oil which will evaporate on contact with the skin or the eyelashes, but whose presence in the cosmetic composition is useful since they facilitate the spreading of the composition when it is applied to the skin or the eyelashes. Such spreading agents, referred to here as volatile solvents or oils, are generally organic compounds having a saturating vapour pressure at 25° C., at least equal to 0.5 millibar (i.e. $0.5\times10^2$ Pa).

The thickener may be selected from organically modified clays, such as monimorillonites and hectorite derivatives, for example bentonite.

The concentration of volatile solvent or organic oil is between 35 and 70% by weight relative to the total weight of the composition. The volatile solvent or organic oil may be selected from isoparaffin, turpentine oil, isopropyl alcohol, ethyl alcohol, white spirit, silicone oils such as hexamethyldisiloxane, cyclopentadimethylsiloxane and cyclotetramethylsiloxane, fluoro oils such as those marketed under the name Galden (Montefluos) or isoparaffin oils such as those which are marketed under the name Isopar (E, G, L or H) and isododecane.

In this embodiment of the invention, the aqueous phase preferably represents from 0.1 to 25% by weight relative to the total weight of the composition.

Reference may be made to WO 91/12793 for the preparation of compositions in the form of a water-in-wax dispersion, these dispersions also having the property of being water-resistant.

The composition according to the invention may also contain ingredients commonly used in cosmetics, such as vitamins, trace elements, softeners, sequestering agents, fragrances, oils, silicones, cohesion agents and basifying or acidifying agents usually used in the cosmetics field, fillers, emollients, usually used in amounts of between 1 and 10%, preserving agents such as, for example, imidazolinyl urea, methylparaben and propylparaben, and fluoro compounds. The composition may also comprise at least one filler such as:

- talc, which is a hydrated magnesium silicate used in the form of particles generally less than 40 microns.
- micas, which are aluminosilicates or varied compositions in the form of flakes from 2 to 200 microns in size, preferably from 5 to 70 microns in size, and from 0.1 to 5 microns thick, preferably from 0.2 to 3 microns thick it being possible for these micas to be of natural origin, such as muscovite, margarite, roscoelite, lipidolite or biotite, or of synthetic origin.
- starch, in particular rice starch,
- kaolin, which is a hydrated aluminum silicate in the form of particles of isotropic form generally less than 30 microns in size,
- zinc and titanium oxides generally used in the form of particles not exceeding a few microns in size,
- calcium carbonate, magnesium carbonate or magnesium hydrocarbonate,
- microcrystalline cellulose,
- silica,
- powders of synthetic polymers such as polyethylene, polyesters (polyethylene isophthalate or terephthalate), polyamides such as those sold under the trade name "Nylon" or "Teflon" and silicone powders.

The compositions according to the invention may in particular be in the form of a mascara or an eye-liner, or may constitute a base for the preparation of mascaras or eyeliners.

Having generally described this invention, a further understanding can be obtained by reference to certain specific examples which are provided herein for purposes of illustration only and are not intended to be limiting unless otherwise specified.

EXAMPLES

In the examples, all the percentages are given by weight of active material.

The cascaras are evaluated by users (6 individuals) for their speed of drying, their immediate adhesion to the eyelash, their staying power over time, their resistance to rubbing (the user rubs her eyelids with the fingers and observes the state of the make-up after rubbing), and the lengthening and weighting which they impart to the eyelashes.

Example 1

A mascara composition according to the invention is prepared by making a homogeneous mixture from the following ingredients:

| | |
|---|---|
| Beeswax | 3% |
| Carnauba wax | 3% |
| Paraffin | 13% |
| Black iron oxide | 7% |
| Triethanolamine stearate | 9% |
| Gum arabic | 3.5% |
| Hydroxyethylcellulose | 1% |
| Oxyethylenated polydimethylsiloxane(*) | 0.6% |
| Sodium polymethacryate | 0.25% |
| Preserving agents | qs |
| Water | qsp |

(*)marketed by the company Dow Corning under the commercial reference Q2-5220

This composition is judged by the users as satisfying all the criteria of choice: it adheres well to the eyelash, dries rapidly, lengthens and weights the eyelash, it has very good staying power and excellent resistance to rubbing (no crumbling observed).

Example 2 (comparative)

| | |
|---|---|
| Beeswax | 3% |
| Carnauba wax | 3% |
| Paraffin | 13% |
| Black iron oxide | 7% |
| Triethanolamine stearate | 9% |
| Gum arabic | 3.5% |
| Hydroxyethylcellulose | 1% |
| Sodium polymethacryate | 0.25% |
| Preserving agents | qs |
| Water | qsp |

A mascara composition is obtained by homogeneous mixing of all the components. Two hours after it is applied, this mascara is evaluated by the users as being satisfactory but inferior to the mascara of Example 1 in terms of speed of drying, lengthening of the eyelash and especially weighting of the eyelashes, staying power over time and resistance to rubbing (a little crumbling observed).

Example 3 (comparative)

| | |
|---|---|
| Beeswax | 3% |
| Carnauba wax | 3% |
| Paraffin | 13% |
| Black iron oxide | 7% |
| Triethanolamine stearate | 9% |
| Gum arabic | 3.5% |
| Hydroxyethylcellulose | 1% |
| Triethyl acetyl citrate | 0.6% |
| Sodium polymethacryate | 0.25% |
| Preserving agents | qs |
| Water | qsp |

A mascara composition is obtained by homogeneous mixing of all the components. Two hours after it is applied, this mascara is evaluated by the users: it is judged as having poor staying power. The resistance to rubbing is very insufficient. The mascara crumbles forming flakes.

Triethyl acetyl citrate is known as a plasticizer for resins, as are certain oxyalkylenated silicones; however, it does not have the properties of oxyalkylenated silicones in the compositions according to the invention.

Example 4 (comparative)

a mascara composition according to the invention is prepared by making a homogeneous mixture from the following ingredients:

| | |
|---|---|
| Beeswax | 3% |
| Carnauba wax | 3% |
| Paraffin | 13% |
| Black iron oxide | 7% |
| Triethanolamine stearate | 9% |
| Oxyethylenated polydimethylsiloxane(*) | 4.75% |
| Preserving agents | qs |
| Water | qsp |

(*)marketed by the company Dow Corning under the commercial reference Q2-5220

It is seen in this example that in the absence of film-forming polymer (replaced by its equivalent weight of Q2-5220) a composition is obtained having a viscosity equivalent to that of water, which cannot be used for make-up. In addition, the pigments are very poorly dispersed.

Comparative tests

The effect of a dimethicone copolyol according to the invention was compared with various plasticizers.

In the composition according to Example 1 described above, the dimethicone copolyol was replaced by its weight equivalent of each of the following plasticizers:

Test 1: 2-ethylhexyl palmitate

Test 2: diisopropyl adipate

Test 3: triethyl acetyl citrate

Test 4: tributyl citrate

Test 5: tripropylene glycol n-butyl ether

The make-up obtained with each of these tests was compared, relative to the composition according to Example 1=control. Each criterion was evaluated between 0 and 3.

0=unsatisfactory criterion

3=entirely satisfactory criterion

The results are outlined in Table I.

TABLE I

| Test | Rate of drying | Weighting | Staying power | Resistance to rubbing | Comments |
|---|---|---|---|---|---|
| Control | 3 | 3 | 3 | 3 | |
| 1 | 0 | 1 | 3 | 0 | does not attach to the eyelash/ uncomfortable |
| 2 | 1 | 0 | 3 | 0 | uncomfortable |
| 3 | 0 | 2 | 0 | 0 | sticks the eyelashes together/poor lengthening/poor curving |
| 4 | 1 | 1 | 3 | 1 | limp eyelashes |
| 5 | 0 | 1 | 0 | 0 | |

It is observed in these tests that, in contrast with dimethicone copolyols, the plasticizers of common use do not allow the desired properties to be obtained.

The subject matter of France priority patent application 96-11878, filed Sep. 30, 1996, is hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A cosmetic composition comprising:

(a) at least one aqueous phase comprising at least one film-forming polymer, (b) at least one fatty phase comprising at least one wax *wherein the wax has a melting point of between 40° and 111° C. and a needle penetration, at 25° C. of between 3 and 40, as measured according to US standard ASTM D 5 or according to French standard AFT 004, and*

*wherein the wax is selected from the group consisting of animal waxes, plant waxes, mineral waxes, synthetic waxes and various fractions of natural waxes, and*

*wherein said synthetic waxes are selected from the group consisting of polyethylene waxes, waxes obtained from Fischer-Tropsch synthesis, silicone waxes, and hydrogenated animal or plant oils,*

(c) at least one silicone selected from the group consisting of:

(i) oxyalkylenated silicones, and (ii) linear polysiloxane-polyoxyalkylene block copolymers.

2. The composition according to claim 1, in the form of an emulsion of the fatty phase in the aqueous phase or a dispersion of the aqueous phase in the fatty phase.

3. The composition according to claim 1, additionally comprising from 0.25 to 25%, by weight relative to the total weight of the composition, of at least one pigment.

4. The composition according to claim 1, wherein the oxyalkylenated silicone has the following formula (I):

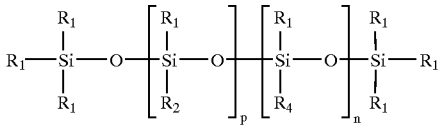

(I)

in which:

$R_1$ and $R_4$, which are identical or different, represent a hydrogen atom, a linear or branched $C_1$–$C_{30}$ alkyl radical or a phenyl radical, $R_2$, which are identical or different, represent $—(C_xH_{2x})—(OC_2H_4)_a—(OC_3H_6)_6—OR_3$, $R_3$ which are identical or different, represent a hydrogen atom, a linear or branched alkyl radical having from 1 to 12 carbon atoms, or a linear or branched acyl radical having from 2 to 12 carbon atoms, n ranges from 0 to 1000, p ranges from 1 to 30, a ranges from 0 to 50, b ranges from 0 to 50, a +b is greater than or equal to 1, x ranges from 1 to 5, the number-average molecular weight being greater than or equal to 15,000.

5. The composition according to claim 4, wherein at least one of the following conditions is satisfied:

$R_1$ and $R_4$ denote a methyl radical, $R_3$ represents a hydrogen atom, a methyl radical or an acetyl radical, p ranges from 8 to 20, a is between 5 and 40, b is between 5 and 40, x is equal to 2 or 3, n ranges from 20 to 600.

6. The composition according to claim 1, wherein the linear polysiloxane-polyoxyalkylene block copolymer contains a polysiloxane block and a polyoxyalkylene block and has formula (II):

$$(\{Y(R_2SiO)_a.R'_2SiYO\}\{(C_n.H_{2n}.O)_{b'}\})_{c'} \quad \text{(II)}$$

in which:

R and R', which are identical or different, represent a monovalent hydrocarbon radical containing no aliphatic unsaturation, n' is an integer between 2 and 4, a' is an integer greater than or equal to 5, b' is an integer greater than or equal to 4, c' is an integer greater than a equal to 4.

Y represents a divalent organic group which is attached to the adjacent silicon atom by a carbon-silicon bond and to a polyoxyalkylene block by an oxygen atom, the number average molecular weight of each polysiloxane block is between about 400 and about 10,000, that of each polyoxyalkylene block being between about 300 and about 10,000, the polysiloxane blocks represent from about 10% to about 90% by weight of the block copolymer, the number average molecular weight of the block copolymer being at least 3000.

[7. The composition according to claim 1, wherein the wax has a melting point of between 60° and 110° C., and a needle penetration, at 25° C., of between 3 and 40, as measured according to US standard ASTM D 5 or according to French standard AFT 004.]

8. The composition according to claim [7] *1*, wherein the wax is solid and rigid at a temperature below 50° C.

9. The composition according to claim 8, containing from 6 to 40% wax, by weight relative to the total weight of the composition.

10. The composition according to claim 1, containing from 0.1 to 25% film-forming polymer by weight relative to the total weight of the composition.

11. The composition according to claim 1, containing from 0.01 to 5% silicone by weight relative to the total weight of the composition.

12. The composition according to claim 1, containing from 10 to 30% silicone by weight relative to the total weight of the film-forming polymer.

13. The composition according to claim 1, in the form of an oil-in-water emulsion.

14. The composition according to claim 13, additionally comprising from 2 to 30% by weight, relative to the total weight of the composition, of at least one emulsifying surfactant.

15. The composition according to claim 14, wherein the surfactant is selected from the group consisting of fatty acids, fatty alcohols, polyethoxylated and polyglycerolated fatty alcohols, fatty acid esters of sucrose, alkyl glucose esters and amine stearates.

16. The composition according to claim 13, containing from 30 to 80% water by weight relative to the total weight of the composition.

17. The composition according to claim 1, in the form of a water-in-wax dispersion.

18. The composition according to claim 17, additionally containing al least one volatile solvent or organic oil.

19. The composition according to claim 17, additionally containing at least one thickener.

20. The composition according to claim 17, wherein the aqueous phase represents from 0.1 to 25% by weight relative to the total weight of the composition.

21. The composition according to claim 1, additionally containing et least one mascara or eye liner additive.

22. A method for making up eyes comprising applying to eyelashes the composition according to claim 1.

23. A method for imparting *better staying power over time and/or improved weighting and/or better resistance to crumbling and/or better lengthening of the eyelashes and/or an improved rate of drying* to a cosmetic composition comprising:

(a) at least one aqueous phase comprising at least one film-forming polymer, (b) at least one fatty phase comprising at least one wax *wherein the wax has a melting point of between 40° and 110° C. and a needle penetration, at 25° C., of between 3 and 40, as measured according to US standard ASTM D 5 or according to French standard AFT 004, and*

*wherein the wax is selected from the group consisting of animal waxes, plant waxes, mineral waxes, synthetic waxes and various fractions of natural waxes, and*

*wherein said synthetic waxes are selected from the group consisting of polyethylene waxes, waxes obtained from Fischer-Tropsch synthesis, silicone waxes, and hydrogenated animal or plant oils*, [better staying power over time and/or improved weighting and/or better resistance to crumbling and/or better lengthening of the eyelashes and/or an improved rate of drying,]

said method comprising adding to said composition a silicone selected from the group consisting of (i) oxyalkylenated silicones, and (ii) linear polysiloxane-polyoxyalkylene block copolymers.

24. The composition according to claim 1, wherein the silicone is an oxyalkylenated silicone that does not have $C_{8-C22}$ alkoxy or alkyl radical linked directly to a silicon atom.

25. The composition according to claim 4, wherein $R_4$ is not hydrophobic.

*26. A cosmetic composition comprising:*

(*a*) *at least one aqueous phase comprising at least one film-forming polymer,*

(*b*) *at least one fatty phase comprising at least one wax,*

(*c*) *at least one silicone selected from the group consisting of:*

(*i*) *oxyalkylenated silicones, and*

(*ii*) *linear polysiloxane-polyoxyalkylene block copolymers, wherein said composition excludes a fluorine-containing waxy polymer.*

* * * * *

UNITED STATES PATENT AND TRADEMARK OFFICE

CERTIFICATE OF CORRECTION

PATENT NO. : RE 38,362 E
DATED : December 23, 2003
INVENTOR(S) : Nathalie Collin et al.

It is certified that error appears in the above-identified patent and that said Letters Patent is hereby corrected as shown below:

Title page,
Item [75], Inventors, "Natalie" should read -- Nathalie --.

Column 10,
Line 11, "111 °c" should read -- 110°c --.
Line 49, "$(OC_3H_6)_6$" should read -- $(OC_3H_6)_b$ --.

Column 11,
Line 22, "a equal" should read -- or equal --.
Line 36, "60°" should read -- 40° --.

Column 12,
Line 7, "al" should read -- at --.
Line 14, "et" should read -- at --.
Line 48, "$C_{8-c22}$" should read -- $C_8$-$C_{22}$ --.

Signed and Sealed this

Thirteenth Day of July, 2004

JON W. DUDAS
*Acting Director of the United States Patent and Trademark Office*